(12) United States Patent
Tiedink et al.

(10) Patent No.: US 7,662,748 B2
(45) Date of Patent: Feb. 16, 2010

(54) FORMULATIONS COMPRISING TRIAZOLES AND ALKOXYLATED AMINES

(75) Inventors: Johannes Gerardus Tiedink, Ugchelen (NL); Emmanuel Philippe Thierry Paris, Herenthout (BE); Mark Arthur Josepha Van der Flaas, Herselt (BE)

(73) Assignee: Janssen Pharmaceutica, N.V., Beerse (BE)

( * ) Notice: Subject to any disclaimer, the term of this patent is extended or adjusted under 35 U.S.C. 154(b) by 630 days.

(21) Appl. No.: 10/503,680

(22) PCT Filed: Feb. 3, 2003

(86) PCT No.: PCT/EP03/01075

§ 371 (c)(1),
(2), (4) Date: Aug. 4, 2004

(87) PCT Pub. No.: WO03/065807

PCT Pub. Date: Aug. 14, 2003

(65) Prior Publication Data

US 2005/0080089 A1    Apr. 14, 2005

(30) Foreign Application Priority Data

Feb. 5, 2002  (EP) ................... 02075466
Dec. 18, 2002 (EP) ................... 02080349

(51) Int. Cl.
*A01N 43/653*  (2006.01)
*A01N 33/02*   (2006.01)
*A61K 31/496*  (2006.01)
*A61K 31/41*   (2006.01)

(52) U.S. Cl. .............. 504/272; 504/118; 514/669; 514/383; 514/397

(58) Field of Classification Search ........ 514/679, 514/546, 383, 254.07, 397, 669; 504/363, 504/272, 118
See application file for complete search history.

(56) References Cited

U.S. PATENT DOCUMENTS

| 4,079,062 | A  | * | 3/1978 | Van Reet et al. .......... 548/268.8 |
| 5,426,121 | A  | * | 6/1995 | Bell .......................... 514/500 |
| 6,383,984 | B1 | * | 5/2002 | Aven ....................... 504/116.1 |

FOREIGN PATENT DOCUMENTS

| EP | 0 393 746 B1 | 6/1994 |
| JP | 60-051102 | 3/1985 |
| JP | 61-151102 | 7/1986 |
| WO | WO 9314630 A1 * | 8/1993 |
| WO | WO 96/10332 | 4/1996 |
| WO | WO 01/05224 A1 | 1/2001 |

* cited by examiner

*Primary Examiner*—Johann R Richter
*Assistant Examiner*—Andriae M Holt
(74) *Attorney, Agent, or Firm*—Woodcock Washburn, LLP

(57) ABSTRACT

The present invention relates to the use of alkoxylated amines to enhance the activity of fungicidal formulations comprising fungicidal triazoles. It also relates to formulations comprising one or more fungicidal triazoles and alkoxylated amines. These formulations are useful for the protection of any living or non-living material, such as crops, plants, fruits, seeds, objects made of wood, thatch or the like, biodegradable material and textiles against deterioration due to the action of fungi.

12 Claims, No Drawings

FORMULATIONS COMPRISING TRIAZOLES AND ALKOXYLATED AMINES

This application is a national stage application for PCT/EP03/01075 filed under 35 U.S.C. 371, filed Feb. 3, 2003.

The present invention relates to the use of alkoxylated amines to enhance the activity of fungicidal formulations comprising fungicidal triazoles. It also relates to formulations comprising one or more fungicidal triazoles and alkoxylated amines. These formulations are useful for the protection of any living or non-living material, such as crops, plants, fruits, seeds, objects made of wood, thatch or the like, biodegradable material and textiles against deterioration due to the action of fungi.

Various classes of compounds are known as antimicrobial and in particular antifungal compounds. Among these classes, the group of fungicidal triazoles is of particular interest and several of such compounds are now widely used as antimicrobials and in particular as antifungals.

Wood preservative formulations have been described in EP-0,393,746 which discloses synergistic combinations of tebuconazole and propiconazole useful for protecting wood, wood-products and biodegradable materials from fungal attack and destruction. WO-96/10332 discloses liquid wood preservation formulations comprising complexes formed by reacting a copper cation and an alkoxylated diamines. JP-60-051102 and JP-61-151102 disclose the use of alkoxylated amines and diamines for stabilizing formulations comprising 1H-1,2,4-triazole-1-ethanimidothioic acid fungicides such as imibenconazole.

As with most individual active ingredients, fungicidal triazoles by themselves do not provide protection against all fungi, bacteria, and other microorganisms which it is desirous to protect any living or non-living material, such as crops, plants, fruits, seeds, objects made of wood, thatch or the like, biodegradable material and textiles against.

Surprisingly, it has been found that by addition of alkoxylated amines of formula (I), the efficacy of formulations comprising fungicidal triazoles is significantly increased. Therefore the fungicidal formulations of the present invention comprise one or more fungicidal triazoles and alkoxylated amines of formula (I) to increase the efficacy or performance, and a carrier.

According to one aspect of the present invention, fungicidal compositions are provided comprising, within certain broad limits of composition (i.e. in certain respective proportions or amounts of the active ingredients) easily determinable by those skilled in the art, the combination of one or more fungicidal triazoles plus alkoxylated amines of formula (I) in synergistic proportions, and a carrier.

Fungicidal triazoles are meant to include
azaconazole 1-[[2-(2,4-dichlorophenyl)-1,3-dioxolan-2-yl]methyl]-1H-1,2,4-triazole,
bromuconazole 1-[[4-bromo-2-(2,4-dichlorophenyl)tetrahydro-2-furanyl]methyl]-1H -1,2,4-triazole
cyproconazole α-(4-chlorophenyl)-α-(1-cyclopropylethyl)-1H-1,2,4-triazole-1-ethanol,
difenoconazole 1-[[2-[2-chloro-4-(4-chlorophenoxy)phenyl]-4-methyl-1,3-dioxolan-2-yl]methyl]-1H-1,2,4-triazole,
epoxiconazole 1-[[(2R,3S)-3-(2-chlorophenyl)-2-(4-fluorophenyl)oxiranyl]methyl]-1H-1,2,4-triazole,
fenbuconazole α-[2-(4-chlorophenyl)ethyl]-α-phenyl-1H-1,2,4-triazole-1-propanenitrile,
fluquinconazole 3-(2,4-dichlorophenyl)-6-fluoro-2-(1H-1,2,4-triazol-1-yl)-4(3H) -quinazolinone,
flusilazole 1-[[bis(4-fluorophenyl)methylsilyl]-methyl]-1H-1,2,4-triazole,
hexaconazole α-butyl-α-(2,4-dichlorophenyl)-1H-1,2,4-triazole-1-ethanol,
ketoconazole 1-acetyl-4-[4-[[[(2R,4S)-2-(2,4-dichlorophenyl)-2-(1H-imidazol -1-ylmethyl)-1,3-dioxolan-4-yl]methoxy]phenyl]-piperazine
metconazole 5-[(4-chlorophenyl)methyl]-2,2-dimethyl-1-(1H-1,2,4-triazol-1-ylmethyl)-cyclopentanol,
penconazole 1-[2-(2,4-dichlorophenyl)pentyl]-1H-1,2,4-triazole,
propiconazole 1-[[2-(2,4-dichlorophenyl)-4-propyl-1,3-dioxolan-2-yl]methyl]-1H -1,2,4-triazole,
tebuconazole α-[2-(4-chlorophenyl)ethyl]-α-(1,1-dimethylethyl)-1H-1,2,4-triazole -1-ethanol,
tetraconazole 1-[2-(2,4-dichlorophenyl)-3-(1,1,2,2-tetrafluoroethoxy)propyl]-1H -1,2,4-triazole,
triticonazole 5-(4-chlorophenyl)methylene)-2,2-dimethyl-1-(1H-1,2,4-triazol-1-ylmethyl)cyclopentanol.

Compositions according to the invention may contain more than one triazole compound, for example, they may contain two or more triazoles selected from azaconazole, propiconazole, cyproconazole, flusilazole, and tebuconazole, or a mixture of cyproconazole and propiconazole, or a mixture of tebuconazole, propiconazole and cyproconazole.

The fungicidal triazoles may be present in their base form or in a salt form, the latter being obtained by reaction of the base form with an appropriate acid. Appropriate acids comprise, for example, inorganic acids, such as the hydrohalic acids, i.e. hydrofluoric, hydrochloric, hydrobromic and hydroiodic, sulfuric acid, nitric acid, phosphoric acid, phosphinic acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The term salt form of a fungicidal triazole also comprises metal complexes which said fungicidal triazole may form. One of the components may occur as a complex and the other not; or both components may occur as a complex. Metal complexes as mentioned above consist of a complex formed between one or more molecules of the active ingredient and one or more organic or inorganic metal salt or salts. Examples of said organic or inorganic salts comprise the halogenides, nitrates, sulfates, phosphates, acetates, trifluoroacetates, trichloroacetates, propionates, tartrates, sulfonates, e.g. methylsulfonates, 4-methylphenylsulfonates, salicylates, benzoates and the like of the metals of the second main group of the periodical system, e.g. the magnesium or calcium salts, of the third or fourth main group, e.g. aluminium, tin, lead as well as the first to the eighth transition groups of the periodical system such as, for example, chromium, manganese, iron, cobalt, nickel, copper, zinc and the like. Preferred are the metals pertaining to the transition elements of the fourth period. The metals may be present in each of their possible valences. The metal ions may be present in any of their possible valences, the most preferred metal copper being most advantageously used in its divalent form Cu(II). Suitable copper compounds are copper sulfate, acetate, hydroxide, oxide, borate, fluoride and in particular copper hydroxide carbonate $Cu(OH)_2CuCO_3$. The complexes can be mono- or polynuclear, they may contain one or more parts of the organic molecule as ligands.

Wherever the term "fungicidal triazole" is used, it is meant to include said compound both in its base or in its salt form, the latter being obtained by reaction of the base form with an appropriate acid. The term salt form as used hereinabove also comprises the solvates which fungicidal triazoles are able to form. Examples of such solvates are e.g., the hydrates, alcoholates and the like.

The fungicidal triazoles for use in the compositions according to the present invention should preferably be present in a substantially pure form, i.e. free from chemical impurities (such as co-products or residual solvents) resulting from their manufacturing and/or handling processes in view to safely control the fungicidal management programs for which they are intended. The term "substantially pure" means a chemical purity, as determined by methods conventional in the art such as high performance liquid chromatography methods, of at least about 96%, preferably at least 98% and more preferably at least 99%.

The alkoxylated amines of formula (I) have the following general formula

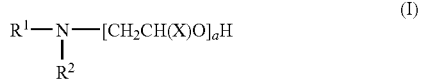

(I)

wherein $R^1$ is a $C_{8-20}$alkyl;

$R^2$ is $-[CH_2CH(X)O]_bH$ (a-1)

or

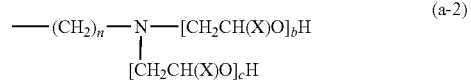

(a-2)

n is an integer from 1 to 4;

each a, b, and c independently are integers which can be 1 to 20;

each X independently is selected from the group consisting of hydrogen, methyl, ethyl, and phenyl.

A group of interesting compounds of formula (I) are those compounds of formula (I) wherein each a, b, and c independently are integers which can be 1 to 6.

A first particular group of alkoxylated amines of formula (I) are those compounds of formula (I) wherein $R^2$ represents radical (a-1).

A second particular group of alkoxylated amines of formula (I) are those compounds of formula (I) wherein $R^2$ represents radical (a-2).

More particular alkoxylated amines of formula (I) are those alkoxylated amines of formula (I) wherein one or more of the following restrictions apply:

a) n is an integer 2 or 3, preferably n is 3;

b) X is hydrogen;

c) R is a $C_{10-20}$alkyl, preferably cocoalkyl or tallowalkyl.

Preferred alkoxylated amines of formula (I) are listed in the following table:

| Product name | Chemical name | CAS number |
| --- | --- | --- |
| Propoduomeen C/13 | N,N',N'-tris(2-hydroxypropyl)-N-cocoalkyl-1,3-diaminopropane | — |
| Ethoduomeen T/11 | mono-(2-hydroxyethyl)-N-tallowalkyl-1,3-diaminopropane | 61790-85-0 |
| Ethoduomeen T/13 | N,N',N'-tris-(2-hydroxyethyl)-N-tallowalkyl-1,3-diaminopropane | 90367-27-4 |
| Ethoduomeen T/25 | N,N',N'-polyoxyethylene(15)-N-tallowalkyl-1,3-diaminopropane | 61790-85-0 |
| Ethoduomeen C/13 | N,N',N'-tris(2-hydroxyethyl)-N-cocoalkyl-1,3-diamino-propane | 90367-21-8 |

Most preferred alkoxylated amine of formula (I) is N,N',N'-tris(2-hydroxyethyl)-N-cocoalkyl-1,3-diamino-propane.

The relative proportions of the one or more fungicidal triazoles and alkoxylated amines of formula (I) in the embodied fungicidal compositions are those proportions which result in unexpected enhanced efficacy, preferably synergistic, against fungi, when compared to a composition including, as an active ingredient, either one or more fungicidal triazoles alone or alkoxylated amines of formula (I) alone. As will readily be understood by those skilled in the art, the said enhanced efficacy may be obtained within various proportions of the one or more fungicidal triazoles and alkoxylated amines of formula (I) in the fungicidal composition, depending on the kind of fungus towards which efficacy is measured and the substrate to be treated. As a general rule, however, it may be said that for most fungi the suitable proportions by weight of the amount of the one or more fungicidal triazoles to alkoxylated amines of formula (I) in the active composition should lie in the range from 5:1 to 1:200, suitably from 5:1 to 1:50, preferably from 2:1 to 1:20, more preferably from 1:1 to 1:10. Specific ratio's (w/w) of fungicidal triazole over alkoxylated amines of formula (I) are 1:160, 1:80, 1:40, 1:20, 1:10 and 1:5.

The amount of each of the active ingredients, i.e. one or more fungicidal triazoles and alkoxylated amines, in the compositions according to the present invention will be so that an effective fungicidal effect is obtained. In particular it is contemplated that the ready to use compositions of the present invention comprise one or more fungicidal triazoles in a range from 0.01% (w/v) to 10% (w/v), preferably from 0.1% (w/v) to 1.5% (w/v). Alkoxylated amines of formula (1) in such ready to use compositions are present in a range from 0.1% (w/v) to 40% (w/v), preferably from 0.5% (w/v) to 10% (w/v). Said ready to use compositions may be obtained by diluting a concentrated composition with an appropriate diluent such as e.g. water.

The fungicidal compositions according to the present invention possess advantageous curative, preventive and systemic fungicidal activity to protect plants, in particular culture plants. The present compositions can be used to protect plants or parts of plants, e.g. fruits, blossoms, flowers, foliage, stems, roots, tubers of plants or culture plants infected, harmed or destroyed by microorganisms, whereby latergrowing parts of plants are protected against such microorganisms.

The compositions according to the present invention show systemic activity. They can further be used in seed disinfection (fruits, tubers, cereal grains) and to treat plant cuttings as well as to combat phytopathogenous fungi occurring in the soil. The compositions of the present invention are particularly attractive due to their good plant tolerance and lack of environmental problems (low application rates).

As examples of the wide variety of culture plants in which the fungicidal compositions according to the present invention can be used, there may be named for example cereals, e.g. wheat, barley, rye, oats, rice, sorghum and the like; beets, e.g. sugar beet and fodder beet; pome and stone fruits and berries, e.g. apples, pears, plums, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes; fibrous plants, e.g. cotton, flax, hemp, jute; citrus fruits, e.g. orange, lemon, grapefruit, mandarin; vegetables, e.g. spinach, lettuce, asparagus, brassicaceae such as cabbages and turnips, carrots, onions, tomatoes, potatoes, hot and sweet peppers; laurel-like plants, e.g. avocado, cinnamon, camphor tree; or plants such as maize, tobacco, nuts, coffee, sugar-cane, tea, vines, hops, bananas, rubber plants, as well as ornamental plants, e.g. flowers, shrubs, deciduous trees and evergreen trees such as conifers. This enumeration of culture plants is given with the purpose of illustrating the invention and not to delimiting it thereto.

A particular mode of administering an fungicidal composition according to the present invention is the administration to the aboveground parts of plants, in particular to the leaves thereof (leaf-application). The number of applications and the administered doses are chosen in accordance with the biological and climatic conditions of life of the causative agent. The fungicidal compositions though, can also be applied to the soil and get into the plants through the root system (systemic activity), in case the locus of the plants is sprayed with a liquid composition or if the components are added to the soil in a solid formulation e.g. in the form of a granulate (soil application).

The fungicidal compositions of the present invention are particularly useful in post-harvest treatment of fruits, especially citrus fruits. In the latter instance, the fruits will be sprayed with or dipped or drenched into a liquid formulation or the fruit may be coated with a waxy composition. The latter waxy composition conveniently is prepared by thoroughly mixing a suspension concentrate with a suitable wax. The formulations for spray, dip or drench applications may be prepared upon dilution of a concentrate such as, e.g. an emulsifiable concentrate, a suspension concentrate or a soluble liquid, with an aqueous medium. Such concentrate in most instances consists of the active ingredients, a dispersing or suspending agent (surfactant), a thickening agent, a small amount of organic solvent, a wetting agent, optionally some anti-freeze agent, and water.

The fungicidal compostions of the present invention can also be used for protecting seed against fungi. To that effect the present fungicidal compositions can be coated on seed as a seed dressing, in case the seed grains seed are drenched consecutively with a liquid composition of the active ingredients or if they are coated with a previously combined composition.

The fungicidal compositions of the present invention are useful in the preservation of wood, wood products, and biodegradable materials and protect said materials against fungal attack and destruction. As wood or wood products which can be preserved with the fungicidal compositions according to the present invention is considered, for example, wood products such as timber, lumber, railway sleepers, telephone poles, fences, wood coverings, wicker-work, windows and doors, plywood, particle board, waferboards, chipboard, joinery, timber used above ground in exposed environments such as decking and timber used in ground contact or fresh water or salt water environments, bridges or wood products which are generally used in housebuilding, construction and carpentry. As biodegradable materials besides wood which can benefit from treatment with the formulations of the invention include cellulosic material such as cotton. Also, leather, textile materials and even synthetic fibres, hessian, rope and cordage.

Wood which is preserved from staining, discoloring and decay is meant to be protected from for example, moulding, rotting, loss of its useful mechanical properties such as breaking strength, resistance to shock and shearing strength, or decrease of its optical or other useful properties due to the occurrence of odour, staining and spot formation. These phenomena are caused by a number of micro-organisms of which the following are typical examples:

Wood-Discoloring Fungi:
1: Ascomycetes:
  Ceratocystis e.g. *Ceratocystis minor.*
  Aureobasidium e.g. *Aureobasidium pullulans*
  Sclerophoma e.g. *Sclerophoma pithyophila*
  Cladosporium e.g. *Cladosporium herbarum*
2: Deuteromycetes:
  *Fungi imperfecti*
  Aspergillus e.g. *Aspergillus niger*
  Dactylium e.g. *Dactylium fusarioides*
  Penicillium e.g. *P. brevicaule, P. variabile, P. funiculosum* or *P. glaucum*
  Scopularia e.g. *Scopularia phycomyces*
  Trichoderma e.g. *Trichoderma viride* or *Trichoderma lignorum.*
  Alternaria e.g. *Alternaria tenius, Alternaria alternata*
3: Zygomycetes:
  Mucor e.g. *Mucor spinorus.*

Wood-Destroying Fungi
1: Soft-rot Fungi:
  Chaetomium e.g. *Ch. globosum* or *Ch. alba-arenulum*
  Humicola e.g. *Humicola grisea*
  Petriella e.g. *Petriella setifera*
  Trichurus e.g. *Trichurus spiralis.*
2: White and brown rot Fungi:
  Coniophora e.g. *Coniophora puteana*
  Coriolus e.g. *Coriolus versicolor*
  Donkioporia e.g. *Donkioporia expansa*
  Glenospora e.g. *Glenospora graphii*
  Gloeophylium e.g. *Gl. abietinum, Gl. adoratum, Gl. protactum,*
  *Gl. sepiarium* or *Gl. trabeum*
  Lentinus e.g. *L. cyathiformes, L. edodes, L. lepideus, L. grinus* or *L. squarrolosus*
  Paxillus e.g. *Paxillus panuoides*
  Pleurotus e.g. *Pleurotis ostreatus*
  Poria e.g. *P. monticola, P. placenta, P. vaillantii* or *P. vaporaria*
  Serpula (Merulius) e.g. *Serpula himantoides* or *Serpula lacrymans*
  Stereum e.g. *Stereum hirsutum*
  Trychophyton e.g. *Trychophyton mentagrophytes*
  Tyromyces e.g. *Tyromyces palustris.*

In order to protect wood from decay it is treated with a fungicidal composition of the present invention. Such treatment is applied by several different procedures such as, for example, by treating the wood in closed pressure or vacuum systems, in thermal or dip systems and the like, or by a wide variety of surface treatments, e.g. by spraying, atomizing, dusting, scattering, pouring, brushing, dipping, soaking or impregnating the wood with a fungicidal composition of the present invention.

The present invention provides a method of preserving wood, wood products or biodegradable materials which comprises applying to said wood, wood products or biodegradable materials a fungicidal composition comprising one or more fungicidal triazoles, alkoxylated amines of formula (I), and a carrier. In a further aspect a method is provided of preserving wood, wood products or biodegradable materials which comprises applying to said wood, wood products or biodegradable materials a fungicidal composition comprising the combination of one or more fungicidal triazoles plus alkoxylated amines of formula (I) in synergistic proportions, and a carrier.

The fungicidal compositions of the present invention comprise one or more fungicidal triazoles plus alkoxylated amines of formula (I), and a carrier. These carriers are any material or substance with which said fungicidal compositions are formulated in order to facilitate their application/dissemination to the locus to be treated, for instance by dissolving, dispersing, or diffusing the said compositions, and/or to facilitate their storage, transport or handling without imparing their antifungal effectiveness. Said acceptable carriers may be a solid or a liquid or a gas which has been compressed to form a liquid, i.e. the compositions of this invention can suitably be used as concentrates, emulsions, solutions, granulates, dusts, sprays, aerosols, pellets, or powders. In many instances the fungicidal compositions of the present invention to be used directly can be obtained from concentrates, such as e.g. emulsifiable concentrates, suspension concentrates, or soluble concentrates, upon dilution with aqueous or organic media, such concentrates being intended to be covered by the term composition as used in the definitions of the present invention. Such concentrates can be diluted to a ready to use mixture in a spray tank shortly before use. Preferably the compositions of the invention should contain from about 0.01 to 95% by weight of the combination of one or more fungicidal triazoles plus alkoxylated amines of formula (I). More preferably this range is from 0.1 to 90% by weight. Most preferably this range is from 1 to 80% by weight, depending on the type of formulation to be selected for specific application purposes.

An emulsifiable concentrate is a liquid, homogeneous formulation comprising one or more fungicidal triazoles plus alkoxylated amines of formula (I) to be applied as an emulsion after dilution in water. A suspension concentrate is a stable suspension of the active ingredients in a fluid intended for dilution with water before use. A soluble concentrate is a liquid, homogeneous formulation to be applied as a true solution of the active ingredients after dilution in water.

The fungicidal compositions of the present invention can also be formulated as waxes for use as a cover or coating of e.g. fruits, in particular citrus fruits.

Appropriate carriers and adjuvants for use in the compositions of the present invention may be solid or liquid and correspond to suitable substances known in the art of formulation, such as, for example natural or regenerated mineral substances, solvents, dispersants, surfactants, wetting agents, adhesives, thickeners, binders, fertilizers or anti-freeze agents.

The fungicidal compositions of the present invention may optionally further comprise quaternary ammonium salts such as quaternary ammonium salts of the trimethyl alkyl ammonium halide type, e.g. trimethyl decyl ammonium chloride, trimethyl dodecylammonium chloride, trimethyl tallow ammonium chloride, trimethyl oleyl ammonium chloride; or of the dimethyl alkyl benzyl ammonium type, e.g. dimethyl decyl benzyl ammonium chloride, dimethyldodecyl benzyl ammonium chloride, dimethyl hexadecylbenzyl ammonium chloride (commonly designated as "cetalkonium chloride"), dimethyl octadecyl benzyl ammonium chloride, dimethyl coco benzyl ammonium chloride, dimethyl tallow benzyl ammonium chloride; and particularly the dimethyl $C_{8-18}$alkyl benzyl ammonium chloride mixture which is commonly known as "benzalkonium chloride"; dimethyl dialkyl ammonium halides, e.g. dimethyl dioctyl ammonium chloride, dimethyl didecyl ammonium chloride, dimethyl didodecyl ammonium chloride, dimethyl dicoco ammonium chloride, dimethyl ditallow ammonium chloride, dimethyl octyl decyl ammonium chloride, dimethyl dodecyl octyl ammonium chloride, dimethyl dihydrogenated tallow ammonium chloride.

As already mentioned the fungicidal compositions of the present invention may further comprise other active ingredients, such as fungicides, bactericides, acaricides, nematocides, insecticides or herbicides, in particular fungicides, for example so as to widen the spectrum of action or to prevent the build up of resistance. In many cases, this results in synergistic effects, i.e. the activity of the mixture exceeds the activity of the individual components.

As biocidal agents, which may be used in combination with the fungicidal formulations of the present invention there may be considered products of the following classes:

Fungicides:

3-iodo-2-propynyl butyl carbamate, 2-aminobutane; 2-anilino-4-methyl-6-cyclopropyl-pyrimidine; 2,6-dichloro-N-(4-trifluoromethylbenzyl)benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, benalaxyl, benodanil, benomyl, binapacryl, biphenyl, bitertanol, blasticidin-S, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyprofuram, dichlorophen, diclobutrazol, diclofluanid, diclomezin, dicloran, diethofencarb, dimethirimol, dimethomorph, dinocap, diphenylamine, dipyrithion, ditalimfos, dithianon, dodine, drazoxolon, edifenphos, ethirimol, fenarimol, fenfuram, fenitropan, fenpiclonil, fenpropidin, fenpropimorph, fentin acetate, fentin hydroxide, ferbam, ferimzone, fluazinam, fludioxonil, fluoromide, flusulfamide, flutolanil, flutriafol, folpet, fosetyl-aluminium, fthalide, furalaxyl, furmecyclox, guazatine, hexachlorobenzene, hymexazol, imazalil, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, pencycuron, phosdiphen, pimaricin, piperalin, polyoxin, prochloraz, procymidone, propamocarb, propineb, pyrazophos, pyrifenox, pyrimethanil, pyroquilon, quintozene (PCNB), sulphur and sulphur preparations, tecloftalam, tecnazene, thiabendazole, thicyofen, thiophanate-methyl, thiram, tolclophos-methyl, tolylfluanid, triadimefon, triadimenol, triazoxide, trichlamide, tridemorph, triflumizole, triforine, validamycin A, vinclozolin, zineb, ziram; isothia- and benzisothiazolone derivatives such as, e.g. 1,2-benzisothiazolone (BIT); oxathiazines such as bethoxazin (i.e. 3-(benzo[b]thien-2-yl)-5,6-dihydro-1,4,2-oxathiazine,-4oxide); strobilurines such as azoxystrobin, metominostrobin, pyraclostrobin, kresoxim-methyl, trifloxystrobin, and picoxystrobin.

Bactericides:

bronopol, dichlorophen, nitrapyrin, nickel dimethyldithiocarbamate, kasugamycin, octhilinone, furanecarboxylic acid, oxytetracyclin, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis*, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos chlorfenvinphos, chlorfluazuron, chliormephos, chlorfenapyr, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethnim, pyridaben, pyrimidifen, pyriproxifen, quinalphos, RH 5992, salithion, sebufos, silafluofen, sulfotep, suiprofos, tebufenozid, tebufenpyrad, tebupirimiphos, teflubenzuron, tefluthrin, temephos, terbam, terbufos, tetrachlorvinphos, thiafenox, thiamethoxam, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

Other biocidal agents that may be used in combination with the compounds of the present invention there may be considered products of the following classes: phenol derivatives such as 3,5-dichlorophenol, 2,5-dichlorophenol, 3,5-dibromophenol, 2,5-dibromophenol, 2,5-(resp. 3,5)-dichloro-4-bromophenol, 3,4,5-trichlorophenol, chlorinated hydrodiphenylethers such as, for example, 2-hydroxy-3,2'4'-trichloro-diphenylether, phenylphenol, 4-chloro-2-phenylphenol, 4-chloro-2-benzylphenol, dichlorophene, hexachlorophene; aldehydes such as formaldehyde, glutaraldehyde, salicylaldehyde; alcohols such as phenoxyethanol; antimicrobially active carboxylic acids and their derivatives; organometallic compounds such as tributyltin compounds; iodine compounds such as iodophores, iodonium compounds; mono-, di- and polyamines such as dodecylamine or 1,10-di(n-heptyl)-1,10-diaminodecane; sulfonium- and phosphonium compounds; mercapto compounds as well as their alkali, earth alkaline and heavy metal salts such as 2-mercaptopyridine-N-oxide and its sodium and zinc salt, 3-mercaptopyridazin-2-oxide, 2-mercaptoquinoxaline-1-oxide, 2-mercapto-quinoxaline-di-N-oxide, as well as the symmetrical disulfides of said mercapto compounds; ureas such as tribromo- or trichlorocarbanilide, dichlorotrifluoromethyldiphenylurea; tribromosalicylanilide; 2-bromo-2-nitro-1,3-dihydroxypropane; dichlorobenzoxazolon; and chlorohexidine.

The following examples are intended to illustrate and not to limit the scope of the present invention in all its aspects.

EXAMPLE 1

Efficacy Against Basidiomycetes in a Modified EN 113 Test

Oven dried blocks (40×15×5 mm) of Scots pine (*Pinus sylvestris,* 509 kg/m$^3$) and beech (*Fagus sylvatica,* 637 kg/m$^3$) were vacuum treated with aqueous dilution of a formulation containing 5% propiconazole and 20% N,N',N'-tris(2-hydroxyethyl)-N-cocoalkyl -1,3-diamino-propane. Depending on the amount of the said aqueous dilution uptaken in the treated blocks the amount of active ingredient, i.e. propiconazole and N,N',N'-tris(2-hydroxyethyl)-N-cocoalkyl-1,3-diamino-propane, can be determined and expressed in g/m$^3$ of uptaken active ingredient (g a.i./m$^3$).

The sample blocks were placed in contact with the fungi (*Coniophora puteana,* and *Coriolus versicolor*) for 8 weeks at culture conditions promoting growth of the organisms. Blocks were then cleaned form adhering mycelium and their weight measured after oven drying. The difference between the oven dry weight at the start and end of the experiment are used to calculate the efficiency of the product, expressed as toxic threshold values. Threshold values are defined as two levels, one corresponding to the lowest concentration deemed to adequately protect wood (weight loss is less then 3%) and the other corresponding to the next concentration in the series used, at which the wood is not adequately protected (weight loss is greater than 3%).

TABLE 1

Threshold values (g propiconazole/m$^3$) of a formulation containing 5% propiconazole and 20% N,N',N'-tris(2-hydroxyethyl)-N-cocoalkyl-1,3-diamino-propane

| Fungus | *Coniophora puteana* | *Corilous versicolor* |
|---|---|---|
| threshold value | 58-117 | 105-220 |
| control threshold value* | 188-373 | 331-458 |

*: formulation comprising only propiconazole as active ingredient

The toxic threshold value for N,N',N'-tris(2-hydroxyethyl)-N-cocoalkyl-1,3-diamino-propane can be found in WO-96/10332 in Table 1 on page 10 and, depending on the type of wood and fungus, ranges from 10240 g/m$^3$ to 21080 g/m$^3$.

TABLE 2

Individual data of a formulation against 2 basidiomycetes

| Conc propiconazole (ppm) | Uptake beech/pine (g a.i./m³) | Weight loss (%) for Coniophora | Weight loss (%) for Coriolus |
|---|---|---|---|
| 100 | 54/58 | 20.9 | 13.3 |
| 200 | 105/117 | 1.0 | 8.5 |
| 400 | 220/228 | 0.2 | 0.7 |
| 600 | 328/360 | 0.1 | 0.1 |
| 800 | 449/477 | −0.2 | −0.1 |

EXAMPLE 2

Phytotoxicity and Fungicidal Activity Versus Powdery Mildew (*Erisiphe graminis*) on Wheat Plants Test model: Winter wheat plants, variety Corvus, were sprayed with the test solutions till run off. Treated plants were incubated in the glasshouse and dusted with *Erisiphe graminis* conidia after drying.

Test solutions:

1) aqueous solutions were prepared by diluting a commercial propiconazole formulation "Tilt® 250 EC" until spray solutions were obtained comprising 8, 16, 20, and 24 ppm of propiconazole.
2) aqueous solutions were prepared comprising of 40, 80, 160, 320, 640, 1280, and 2560 ppm of N,N',N'-tris(2-hydroxyethyl)-N-cocoalkyl-1,3-diamino-propane (i.e. ethoduomeen C/13).
3) to aqueous solutions comprising 8 and 16 ppm of propiconazole an amount of "ethoduomeen C/13" was added yielding test solutions wherein the ratio of propiconazole over "ethoduomeen C/13" is 1/160, 1/80, 1/40, 1/20, 1/10 and 1/5.

The commercial "Tilt® 250 EC" formulation comprises 25% (w/v) of propiconazole dissolved in an aromatic petroleum hydrocarbon liquid mixture.

On day 17 after dusting the wheat plants with *Erisiphe graminis* the % inhibition of fungal growth was evaluated.

Results and Conclusions

Control plants are 100% infected with *E. graminis* and propiconazole at 24 ppm was 80% active against *E. graminis*.

A clear increase in fungicidal activity versus *E. graminis* was seen when propiconazole was tested in combination with "ethoduomeen C/13":

combination of 16 ppm propiconazole with "ethoduomeen C/13" at ratio's down to 1/10 were almost completely active (98%) whereas propiconazole at 16 ppm was 50% active.

combination of 8 ppm propiconazole with "ethoduomeen C/13" at ratio's down to 1/10 were about 80% active whereas propiconazole at 8 ppm was 25% active.

TABLE 3

Fungicidal activity versus *E. graminis* of combination formulations propiconazole/"ethoduomeen C/13" on wheat plants. The % inhibition is the mean of 4 replicates.

| Compound conc (ppm a.i.) | | | % Fungicidal activity |
|---|---|---|---|
| propiconazole | ethoduomeen C/13 | ratio | versus *E. graminis* |
| 24 | 0 | — | 80 |
| 20 | 0 | — | 50 |
| 16 | 0 | — | 50 |
| 8 | 0 | — | 25 |
| 0 | 2560 | — | 0 |
| 0 | 1280 | — | 0 |
| 0 | 640 | — | 0 |
| 0 | 320 | — | 0 |
| 0 | 16 | — | 0 |
| 0 | 80 | — | 0 |
| 0 | 40 | — | 0 |
| 16 | 2560 | 1/160 | 98 |
| 16 | 1280 | 1/80 | 98 |
| 16 | 640 | 1/40 | 98 |
| 16 | 320 | 1/20 | 98 |
| 16 | 160 | 1/10 | 98 |
| 16 | 80 | 1/5 | 90 |
| 8 | 1280 | 1/160 | 80 |
| 8 | 640 | 1/80 | 70 |
| 8 | 320 | 1/40 | 85 |
| 8 | 160 | 1/20 | 85 |
| 8 | 80 | 1/10 | 70 |
| 8 | 40 | 1/5 | 50 |
| control water | — | — | 0 |

The invention claimed is:

1. A fungicidal composition consisting of:

one or more fungicidal triazoles selected from azaconazole, bromuconazole, cyproconazole, difenoconazole, epoxiconazole, fenbuconazole, fluquinconazole, flusilazole, hexaconazole, ketoconazole, metconazole, penconazole, propiconazole, tebuconazole, tetraconazole, and triticonazole;

at least one alkoxylated amine of formula (I):

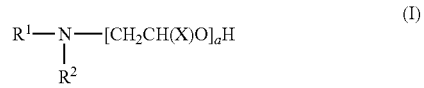

wherein $R^1$ is a $C_{8\text{-}20}$alkyl;

$R^2$ is

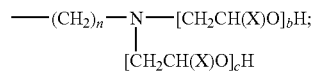

n is an integer from 1 to 4;

each a, b, and c independently are integers which are 1 to 20;

each X is phenyl; and one or more optional ingredients selected from carriers, quaternary ammonium salts, fungicides, bactericides, acaricides, nematocides, insecticides, and herbicides.

2. The composition according to claim 1 wherein the fungicidal triazole is propiconazole.

3. The composition according to claim 1 wherein the fungicidal triazole is a mixture of cyproconazole and propiconazole.

4. The composition according to claim 1 wherein the ratio of the fungicidal triazole to the at least one alkoxylated amine is from 5:1 to 1:200.

5. The composition according to claim 2 wherein the ratio of the fungicidal triazole to the at least one alkoxylated amine is from 5:1 to 1:200.

6. The composition according to claim 3 wherein the ratio of the fungicidal triazole to the at least one alkoxylated amine is from 5:1 to 1:200.

7. The composition according to claim 4 wherein the ratio is from 2:1 to 1:20.

8. A method forming a fungicidal formulation consisting of:
providing at least one alkoxylated amine of formula (I)

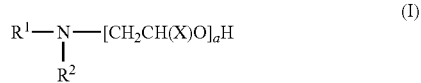
(I)

wherein
$R^1$ is a $C_{8-20}$alkyl;
$R^2$ is

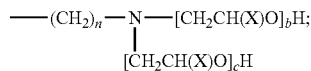

n is an integer from 1 to 4;
each a, b, and c independently are integers which can be 1 to 20;
each X is phenyl;
providing one or more fungicidal triazoles selected from azaconazole, bromuconazole, cyproconazole, difenoconazole, epoxiconazole, fenbuconazole, fluquinconazole, flusilazole, hexaconazole, ketoconazole, metconazole, penconazole, propiconazole, tebuconazole, tetraconazole, and triticonazole;
providing one or more optional ingredients selected from carriers, quaternary ammonium salts, fungicides, bactericides, acaricides, nematocides, insecticides, and herbicides; and
combining the at least one alkoxylated amine, the one or more fungicidal triazoles, and the one or more optional ingredients.

9. The method according to claim 8 wherein the fungicidal triazole is propiconazole.

10. The method according to claim 8 wherein the fungicidal triazole is a mixture of cyproconazole and propiconazole.

11. The method according to claim 8 wherein the ratio of the fungicidal triazole to the at least one alkoxylated amine is from 5:1 to 1:200.

12. The method according to claim 11 wherein the ratio is from 2:1 to 1:20.

* * * * *

UNITED STATES PATENT AND TRADEMARK OFFICE
CERTIFICATE OF CORRECTION

PATENT NO.      : 7,662,748 B2                                        Page 1 of 1
APPLICATION NO. : 10/503680
DATED           : February 16, 2010
INVENTOR(S)     : Tiedink et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1071 days.

Signed and Sealed this

Thirtieth Day of November, 2010

David J. Kappos
*Director of the United States Patent and Trademark Office*